United States Patent
Gleeson et al.

(10) Patent No.: US 6,679,904 B2
(45) Date of Patent: Jan. 20, 2004

(54) DEVICE FOR CLOSURE OF PUNCTURE WOUND

(76) Inventors: Malachy Gleeson, Collingwood, South Hill Avenue, Harrow on the Hill, HA1 3PB (GB); James Taylor, 158 Braid Road, Edinburgh, Eh10 6JB (GB); James Coleman, 20 Greenmount Road, Terenure, Dublin 6 (IE)

( * ) Notice: Subject to any disclaimer, the term of this patent is extended or adjusted under 35 U.S.C. 154(b) by 12 days.

(21) Appl. No.: 09/284,664
(22) PCT Filed: Oct. 15, 1997
(86) PCT No.: PCT/GB97/02845
§ 371 (c)(1), (2), (4) Date: Jun. 29, 1999
(87) PCT Pub. No.: WO98/17179
PCT Pub. Date: Apr. 30, 1998

(65) Prior Publication Data
US 2003/0004543 A1 Jan. 2, 2003

(30) Foreign Application Priority Data
Oct. 17, 1996 (GB) ................................. 9621622

(51) Int. Cl.⁷ ................................................ A61B 17/08
(52) U.S. Cl. ..................... 606/219; 606/213; 227/181.1
(58) Field of Search ................................. 606/219, 217, 606/216, 213, 142, 143, 220, 221, 159; 227/175.1, 181.1, 181.2, 175.3, 175.4, 176.1; 600/104

(56) References Cited

U.S. PATENT DOCUMENTS

| | | | |
|---|---|---|---|
| 4,771,782 A | 9/1988 | Millar | 128/637 |
| 4,934,364 A | * 6/1990 | Green | 606/143 |
| 5,131,379 A | * 7/1992 | Sewell, Jr. | 600/104 |
| 5,292,332 A | 3/1994 | Lee | 606/213 |
| 5,306,254 A | * 4/1994 | Nash et al. | 604/168.01 |
| 5,395,030 A | * 3/1995 | Kuramoto et al. | 227/179 |
| 5,527,322 A | 6/1996 | Klein et al. | 606/144 |
| 5,536,251 A | 7/1996 | Evard et al. | 604/93 |
| 5,674,231 A | 10/1997 | Green et al. | 606/142 |
| 5,810,846 A | * 9/1998 | Virnich et al. | 606/142 |
| 5,855,312 A | * 1/1999 | Toledano | 227/176.1 |
| 6,007,563 A | * 12/1999 | Nash et al. | 606/213 |

FOREIGN PATENT DOCUMENTS

| | | | |
|---|---|---|---|
| EP | 0756851 | 2/1997 | A61B/17/128 |
| EP | 0774237 | 5/1997 | A61B/17/00 |
| WO | 9720505 | 6/1997 | A61B/17/00 |

* cited by examiner

Primary Examiner—Michael J. Milano
Assistant Examiner—Julian W. Woo
(74) Attorney, Agent, or Firm—Nutter McClennen & Fish, LLP

(57) ABSTRACT

A surgical stapler for use at visually inaccessible sites comprises a shaft having a stapler head at its distal end and a guide means for accommodating a separate, pre-positioned guide wire whereby the stapler may be slid bodily along the guide wire to guide the stapler head towards the exterior of a blood vessel. A blood vessel locator tube has a forward end projecting forwardly of the stapler head for entering the blood vessel through a puncture site and a rear end remote from the distal end of the shaft. The locator tube allows the positioning of the stapler head at the blood vessel to be indicated by a flow of blood from the rear end of the tube.

12 Claims, 4 Drawing Sheets

DEVICE FOR CLOSURE OF PUNCTURE WOUND

FIELD OF THE INVENTION

The present invention relates to a device for locating and sealing a puncture wound in animal and human tissue and the related method. A particular example is a vascular puncture.

BACKGROUND OF THE INVENTION

An ever increasing number of vascular interventional procedures are being undertaken by cardiologists and radiologists. With the growing use of both diagnostic and therapeutic procedures requiring percutaneous vascular access, a real demand exists for a method and device for accurately locating and closing the puncture site in the blood vessel, post inter-ventional procedure.

Due to ease of access, the most common site selected for these percutaneous arterial inter-ventional procedures is the femoral artery. The normal procedure is to insert an angiographic needle into the femoral artery. This is followed by the insertion of a guide wire and over this guide wire successive dilators are passed percutaneously into the artery in order to widen the puncture in the artery sufficiently to allow the sheath of optimal diameter for the diagnostic or therapeutic procedure to be inserted. Through this sheath is then inserted the required catheter or intervengional device in order to perform the required diagnostic or therapeutic procedure on the patient.

At the end of the procedure above, the standard treatment on removal of the sheath involves digital pressure on the artery, supplemented with external compression such as sandbags, pneumatic extension cuffs, or adjustable vice-like devices which may be graduated to apply different degrees of pressure on the skin over the puncture site. This method results in the occlusion of the puncture site by thrombosis of blood in the wall of the puncture site and haemostasis in the percutaneous tract. It causes considerable discomfort for the patient and is associated with a long period of immobilisation. Unpredictable post-procedural haemorrhaging during time periods varying from hours to days after the intervention are not uncommon, and may even be fatal for the patient. The additional healthcare cost in dealing with this complication may be considerable.

A series of devices have been invented to address some of these problems by Datascope Corp. U.S.A., PerClose Corp. U.S.A., Kensey Nash Corp. U.S.A. and Bard Corp. U.S.A.

SUMMARY OF THE INVENTION

The present invention which is, however, independent of the exact procedure and of which type of wound is involved, discloses a new method and a new device for sealing a tissue wall puncture by approximating the walls of the tissue in such a way as to obliterate the puncture site. The present invention will find use for vascular puncture wounds, as well as in other medical procedures which rely on percutaneous access to hollow organs such as laparo-scopic procedures, arthroscopic procedures, and the like. It will also find use in closing body orifices approached directly by the device or approached through body cavities or organs.

The new method involves the use of a surgical stapler which includes means to permit use at visually inaccessible sites.

Accordingly, the invention proposes a surgical stapler having a stapler head at its distal end, comprising guide means which can be used to constrain the stapler to move along a pre-positioned guide wire to reach a location along the path of said guide wire. The invention is of particular use at visually inaccessible surgical sites.

The invention also proposes a surgical stapler, for use at visually inaccessible vascular sites, having a stapler head at its distal end, and comprising guide means which can be used to constrain the stapler to move along a pre-positioned guide wire to reach a location along the path of said guide wire, and locator means which project forwardly of the stapler head which enable blood flow to be sensed within a blood vessel with consequential location of the stapler head adjacent the exterior of said blood vessel.

After the intervention the guide wire may have an incremental marking measurement scale along its length, allowing the operator to estimate precisely the amount of guide wire which is placed within the blood vessel. After the interventional procedure serial dilators may be placed over the guide wire and used to dilate the subcutaneous tract down to the level of the external wall of the arterial puncture to allow access by the stapler. The dilator may contain a radio-opaque marker and also a measurement scale which allows the accurate measurement of the length of the percutaneous tract from the skin level to the outer surface of the blood vessel puncture site.

As an alternative method of locating the puncture accurately, the dilator may have a fine bore plastic tube running through its length which passes over the guidewire. The calibre of this plastic tubing is such that it will be sufficiently small to pass into the blood vessel. This tubing may be fixed to the dilator and protrudes for approximately 1–6 mm and preferably 2–4 mm beyond the distal end of the tissue tract dilator. When blood is observed pulsing back from the distal end of this tubing on to the skin, it can be taken to signify that the tube has entered the blood vessel and consequently the dilator has reached the outer surface of the blood vessel. When this occurs, the exact depth of the percutaneous tract may be measured. Transmission of a a pulsation via the dilator to operator may be taken as further evidence that the dilator is resting against the outer wall of the artery. After completion of dilation of the tract, the dilator is removed over the guidewire which itself is left in place so that the inventive stapler can then be used.

Alternatively, the fine bore tube may be fixed within the stapler itself with the same degree of projection. In either case, the distal end of the tube may have a longitudinal slit into which the guidewire may enter as it curves into the artery.

BRIEF DESCRIPTION OF THE DRAWINGS

In order that the invention shall be clearly understood, exemplary preferred embodiments are now described with reference to the drawings, in which.

DETAILED DESCRIPTION OF THE INVENTION

Figure 1:
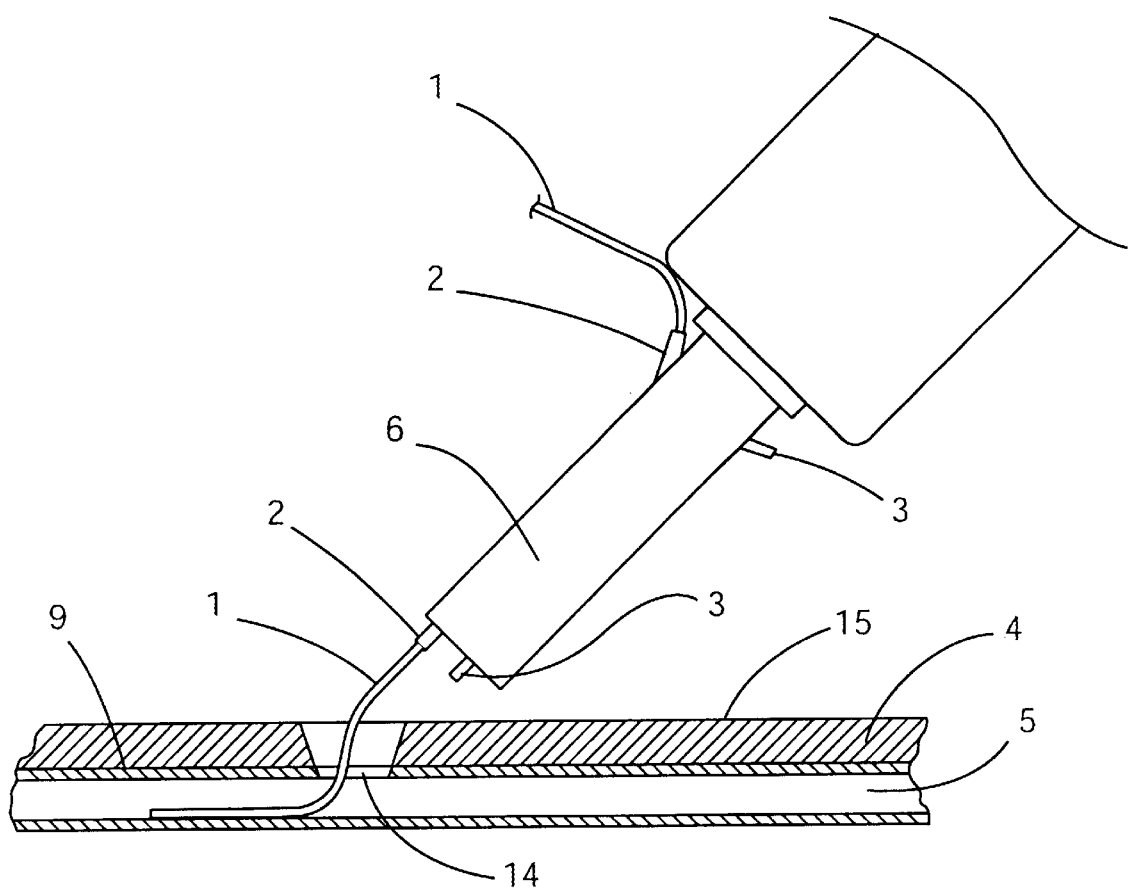
FIG. 1 is a schematic view of an apparatus according to the present invention being moved into position.

A new vascular stapling device is advanced over a guidewire 1 (see FIG. 1) previously inserted. The shaft of the stapling device which may be rigid or flexible slides down along the guidewire through the dilated subcutaneous tissue 4 tract and rests on the wall of the blood vessel 9. The shaft 6 of the stapling device may be calibrated in order to confirm to the operator that the previously measured length of the tract has been travelled by the shaft. Running through the shaft of the stapling device may be one or two blood vessel puncture site locating flexible plastic tubes 2, which may be advanced over the guidewire 1. These tubes may be located in the front and/or behind and/or beside the one or more staples to be delivered to close the puncture site. This plastic tubing may be calibrated and its exact relationship with the tip of the stapling device is known because of calibrated graduated measured markings or other method of marking along its length. In addition this tubing may be radio-opaque further facilitating identifying its position in relation to the puncture site.

Figure 2:
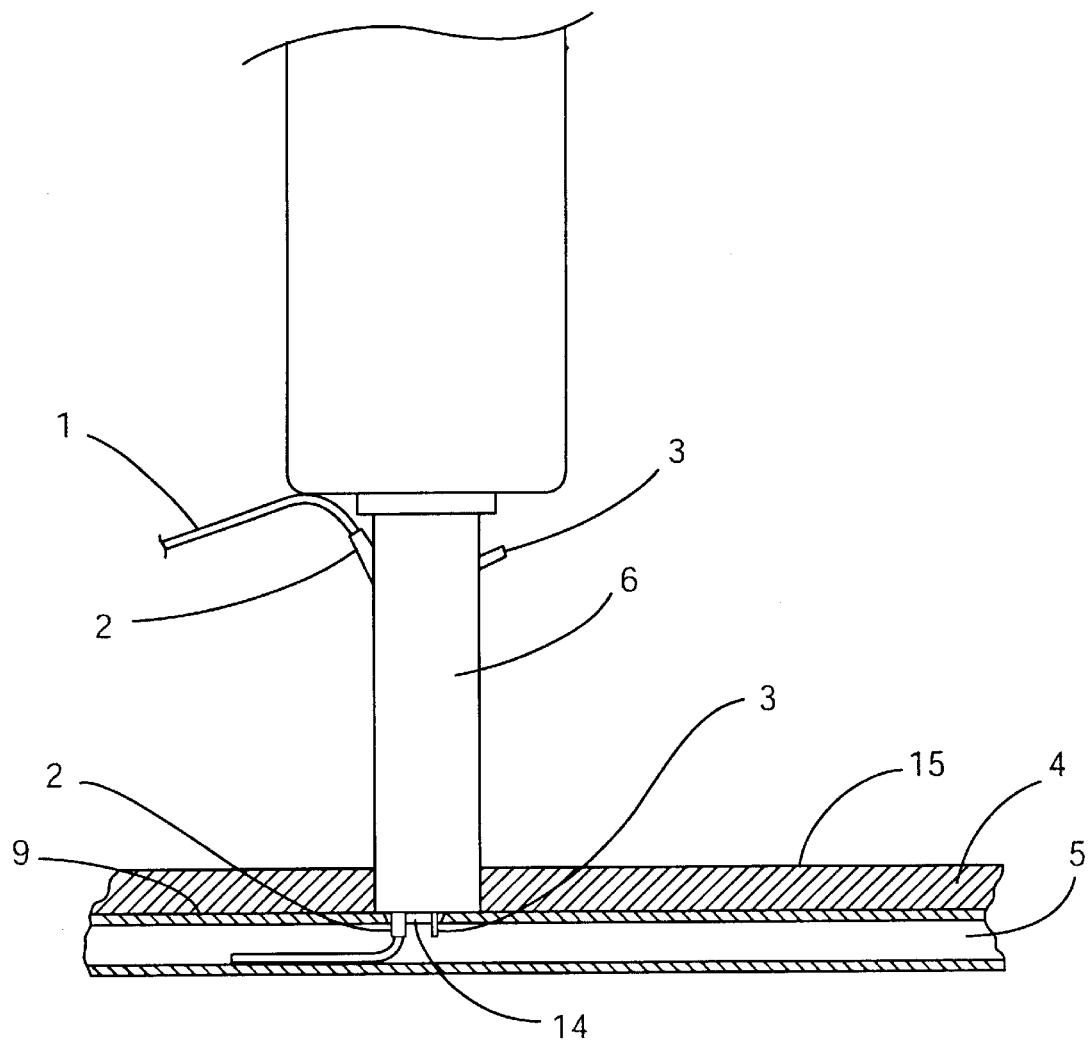
FIG. 2 is a schematic view of the surgical stapling device which has been brought into position for use over the guide wire and its position may be indirectly confirmed by observing the back flow of blood through the blood vessel puncture site locator tubing.

As the distal end of the stapling device (FIG. 2) comes to the outer wall of the blood vessel. 9, an approximate 4 mm protrusion of the blood vessel puncture site locator plastic tubing 2, 3 may enter through the puncture site 14 into the lumen of the blood vessel 5. Pulsating blood will then traverse back through the tubing, through the shaft 6 of the stapling device, and out through the proximal lumen of the tubing 2, 3. This can be taken as an indication that the tip of the stapling device rests against the outer blood vessel wall 9 at the puncture site 14. Transmission of a pulsating feeling from artery via stapler to operator may be taken as further evidence that the stapler is resting against the outer wall of the artery. A second plastic tubing 3 which may be located behind the first or second staple may also be advanced into the arterial puncture to confirm exact localization and alignment of the stapler, if so desired.

Figure 3:
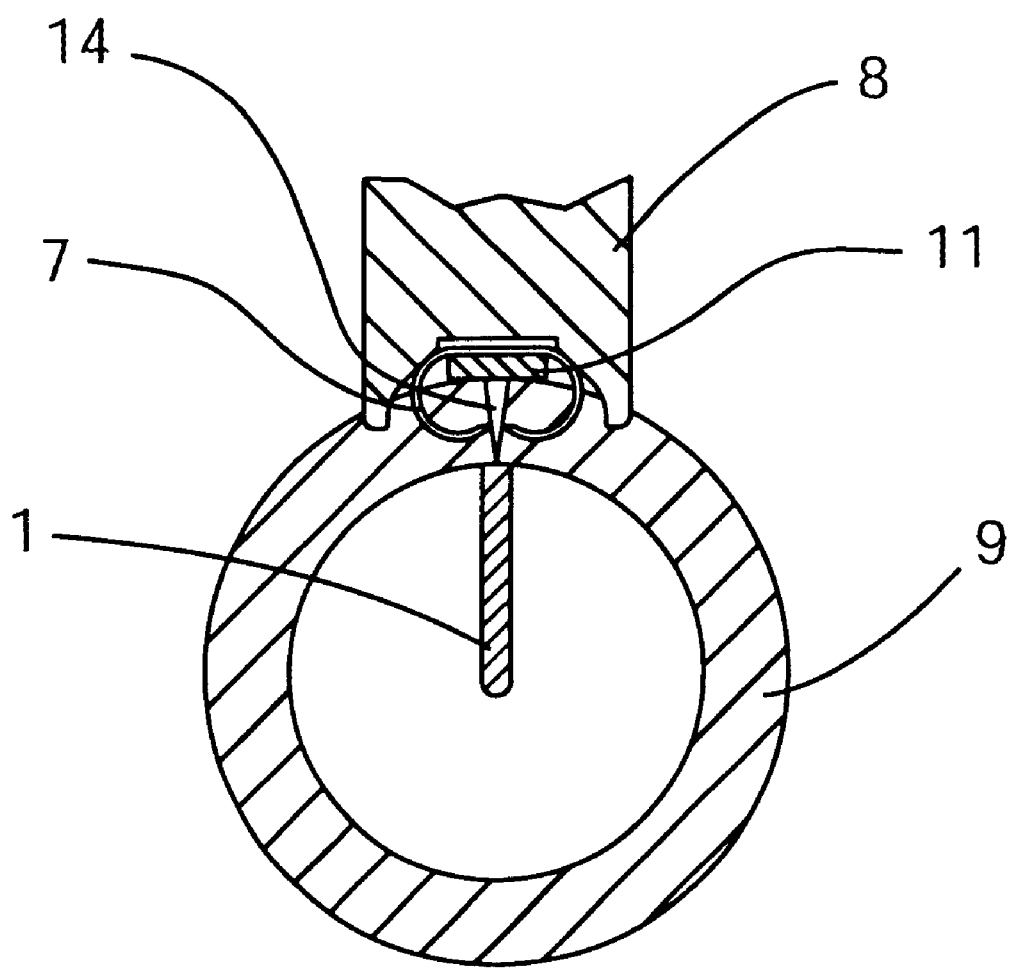
FIG. 3 is a cross-sectional view of an artery with the guide wire and stapler still in place.

Following confirmation of the stapler position, the blood vessel locator tubing 2, may be pulled back along the guide wire 1 into the shaft of the stapler. The pulsation of blood then ceases. At this point the distal end of the stapler which is orientated by the guidewire 1 is now placed firmly against the blood vessel wall 9. As the shaft 6 of the stapling device is brought towards perpendicular position (see FIG. 2) in relation to the skin 15, it will result in the guidewire assuming an angle approaching or greater than 90 degrees and this may cause the puncture hole to be stretched and to change from a round shape to become more oblong. This has the effect of bringing the opposite walls closer together. A safety latch on the handle of the stapler is released and graduated pressure is then applied to the handle of the stapler, which results in the two needle sharp legs (see FIG. 3) of one or more separate staples placed in parallel to be deployed simultaneously (or consecutively, if delivery mechanism is so designed) in order to engage the blood vessel wall. In the case where two staples are delivered, the four staple points (two points per staple) are ejected either in the longitudinal or transverse axis (if stapler is rotated 90 degrees) of the blood vessel and their accurate positioning is assisted by the previous measurements described above and by the fact that the staple delivery system is held on a guide wire. The one or more pre-formed staples may be totally deployed into the wall of the blood vessel 9 while at the same time undergoing a predetermined deformation 7 as defined by the shape of the staple former 8 mechanism in the stapler head.

If required, an angiogram may be performed via a side arm on the plastic tubing which traverses the length of the stapling shaft. Contrast medium may be injected into the blood vessel, provided the tubing is advanced along the guide wire and into the blood vessel. Alternatively, the contrast medium may be injected at the outer surface of the blood vessel if so desired in order to reconfirm the exact positioning of staples. Also a radio opaque marker may be present in the tip and shaft of the stapling device and this combined with the radio opaque nature of the staples themselves may facilitate further confirmation that the desired placement has taken place.

The trigger mechanism which advances the single or double staple pushers (which are part of the staple former mechanism 8) (see FIG. 4) may be further advanced and this results in one or both staples being further deformed to the desired shape and ejected by the formed shape unload spring 12 from the distal end of the stapler simultaneously (or consecutively if stapler so designed), with the transverse member of each staple perpendicular to the long axis of the blood vessel. Alternatively, they may be discharged in parallel to the long axis of the blood vessel resulting in a transverse closure of the puncture site. Closure of the staples will result in the approximation of the opposite walls of the puncture site. The end result will be a minimum of one staple (preferably two) closing the puncture site by means of deformation of two metal or absorbable staples (or staples made from other non-absorbable implantable material) in such a way as to approximate the walls of the puncture site.

During the final closing action of the staples, the operator may decide whether or not to close the puncture site around the guide wire. Normally, the guide wire will be of sufficiently fine calibre so as to result in minimal subsequent problems of bleeding on its removal. The operator may find it desirable to leave the guide wire in place after deployment of the staple or staples if he believes that there is a danger that the vascular procedure which has been carried out will require a re-intervention within a defined time period. If however, the operator is confident that no subsequent intervention in the immediate post-procedure period will be warranted, the guide wire may be removed prior to the final formation of the staple resulting in the closure of the puncture site. Alternatively, the total procedure of deployment, deformation and ejection of the staple or staples from the stapling device may be carried out in one continuous movement over the guidewire which may be removed immediately after deployment.

Two spring-like or other mechanisms 12 will eject the staples either towards the midline of the stapler shaft or towards the lateral walls of the stapler when the final trigger activation squeeze mechanism has been completed. This will result in releasing the staples from the distal end of the stapler and allow withdrawal of the stapler shaft from the percutaneous tract over the guide wire with ease.

Figure 4:
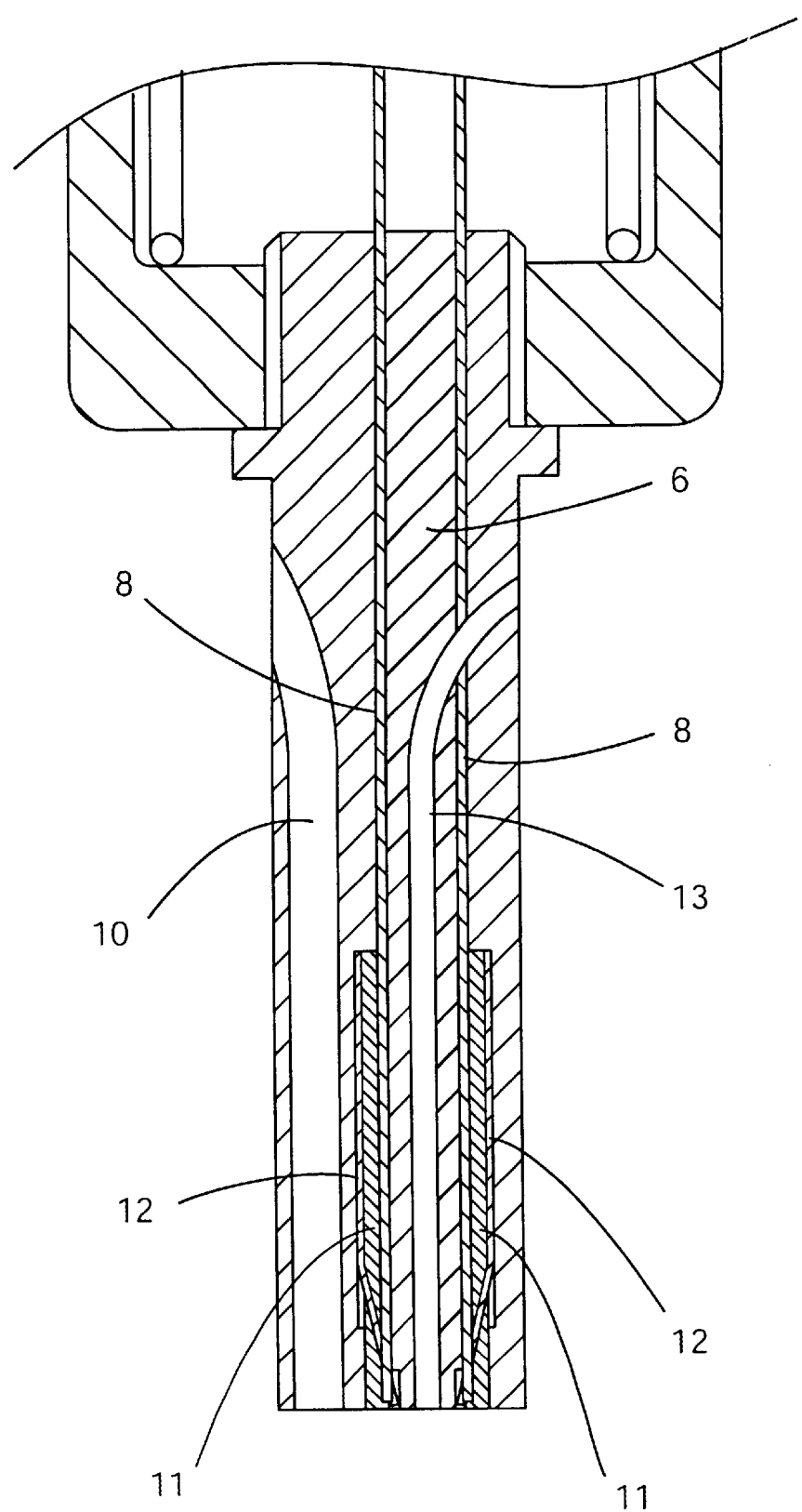
FIG. 4 is a schematic view in section of the distal end of an apparatus constructed according to the present invention.

FIG. 4 illustrates another embodiment of an apparatus having a frame and shaft 6 (which may be flexible) which stores at least one surgical staple at its distal portion. The shaft has at least one purposely built hollow channel 10, 13 (see FIG. 4) running throughout its length which allows the shaft 6 to be advanced over a guide 1 which has previously been placed percutaneously into a blood vessel lumen 5 in order to secure vascular access as previously described for percutaneous intravascular interventions. This purposely built channel (or channels) 10, 13 may also be used to advance blood vessel puncture site locator tubing 2, 3 along guidewire or by itself into blood vessel puncture site 14. The frame and shaft (which has been advanced over the guidewire) house two staple pushing apparatus, each having a staple forming mechanism 8, which advance the staple or staples into the margins of the puncture site on the outer surface of the blood vessel (see FIG. 3). Two anvil means 11 are shown on the distal end of the shaft for closing the staple in a manner that causes the staple to penetrate the wall 9 of the blood vessel. Subsequent deformation of the staple about the anvil 11 will result in the bringing together of the opposite walls of the puncture site. The staple pushing apparatus (of which the staple former 8 may be a part) may extend from the frame through the shaft 6 of the device and may be activated by a trigger mechanism attached to the frame and forming a part thereof.

The surgical staples may be stored in parallel beside each other, with the transverse member of the staple perpendicular to the longitudinal axis of the shaft. The shaft may be rotatable. This point of rotation may begin at the junction between the frame and the shaft. The distal end of the shaft may have a pivoting joint. Throughout the length of the shaft, at least one elongated rod may be positioned within the shaft to act as a pusher to deploy one or preferably two staples simultaneously or consecutively and in parallel while the stapler is positioned over the guide. The means of advancing the staples distally may be controlled by the operator at a proximal location. The distal end of the staple former 8 engages the staple or staples and advances the staple or staples in the distal direction. The staple former which forms the distal end of the staple pusher has at its distal end a plate member, and the plate member may be dimensioned, configured and arranged to engage and advance the staple distally. The staple storage area at the distal end of the shaft includes at least one but preferably two anvils 11 (see FIG. 3) which each engage a staple and deform it to a predetermined configuration.

A surgical staple is adapted to bring together the opposite walls of a puncture site in a blood vessel. The staple may comprise of a length of wire and two perpendicular legs which are joined by a transverse member. These perpendicular legs are sharpened and will penetrate the outer wall of the blood vessel. Deformation of the bridge portion of the staple will result in both legs of the staple deforming in arcuate manner and facing in a direction generally towards the centre of the transverse wire portion. Deformation of the staples occurs over each anvil and results in the shortening of the transverse member which ultimately results in the opposite walls of the puncture site being advanced towards each other. The leg members of the staple are folded in such a manner so as not to interfere with each other. The surgical staple may be made from stainless steel, titanium or any absorbable or non-absorbable implantable polymer, i.e. any suitable metal or non-metal.

On completing the closure mechanism of the stapler handle, the indicator on the handle (if present) may show that the staple closure cycle is complete and on release of the handle, the deforming push rods may retract into the shaft of the stapler. This retraction movement of the push rods may cause a spring 12 or other mechanism on the side of the stapler shaft wall (which was deformed by the advancing staple former) to return to its original shape. This spring-back effect may result in one or both of the fully formed staples being ejected from their housing in the distal end of the stapler. Since the staples are now free of the stapling device nose, the staple device itself may now be easily removed from the percutaneous tract along the guide wire.

The procedure described above may be carried out using a kit comprising of a surgical staple, guide wire, fine bore plastic tubing for performing an angiogram and localizing the position of blood vessel puncture site in relation to the stapler, a dilator with a hollow channel and graduated markings on its outer surface which can be detected radiologically, a connector side arm for the tie bore tubing through which saline or contrast medium may be injected. Components may be supplied as part of a kit or they may be supplied in a blister type or other packaging.

What is claimed is:

1. A surgical stapler for use at visually inaccessible sites, the stapler comprising:

a shaft having
      a staple forming mechanism within a distal end of the shaft and adapted to advance and apply at least one staple,
      a guide means for accommodating a separate, pre-positioned guide wire, the guide wire being effective to slidably receive the stapler as a unit to guide the staple forming mechanism towards the exterior of a blood vessel, and
      a blood vessel locator tube having a forward end which projects forwardly of the staple forming mechanism for entering the blood vessel through a puncture site and a rear end remote from the distal end of the shaft whereby the positioning of the blood vessel locator tube through the puncture site is indicated by the flow of blood from the rear end of the tube.

2. A surgical stapler according to claim 1, wherein the guide means comprises a channel in the shaft, the channel also accommodating the blood vessel locator tube.

3. A surgical stapler according to claim 1, wherein the guide means comprises a first channel in the shaft, the shaft also having a second channel accommodating the blood vessel locator tube.

4. A surgical stapler according to claim 1, wherein the blood vessel locator tube projects beyond the staple forming mechanism by a distance of 1 to 6 mm.

5. A surgical stapler according to claim 1, wherein the staple forming mechanism ejects one or two staples at each actuation.

6. A surgical stapler for use at visually inaccessible sites, the stapler comprising:

a shaft having
      a staple forming mechanism formed on a distal end of the shaft and adapted to advance and apply at least one staple,
      a guide means for accommodating a separate pre-positioned guide wire, the guide wire being effective to slidably receive the stapler as a unit to guide the staple forming mechanism towards the exterior of a blood vessel, and
      a blood vessel locator tube having a forward end which projects forwardly of the staple forming mechanism for entering the blood vessel through a puncture site and a rear end remote from the distal end of the shaft whereby the positioning of the blood vessel locator tube through the puncture site is indicated by the flow of blood from the rear end of the tube, wherein the blood vessel locator tube may be withdrawn into the staple forming mechanism after location of the puncture site.

7. A surgical stapler for use at visually inaccessible sites, comprising:

a shaft having a proximal end, a distal end, and at least one hollow channel extending at least partially therethrough for slidably receiving a pre-positioned guide wire, such that the surgical stapler can be slid along the guide wire to a puncture site in a blood vessel;

a staple applying member within the distal end of the shaft and adapted to advance and apply at least one staple to close at least a portion of a puncture in a blood vessel;

a locator tube mated to the shaft and positioned forwardly of the staple applying member, the locator tube being effective to receive blood flow therethrough to indicate the position of the distal end of the shaft with respect to a puncture site in a blood vessel.

8. The surgical stapler of claim 7, wherein the locator tube includes a distal end positioned distal to the staple applying member, and a proximal end positioned adjacent the proximal end of the shaft.

9. The surgical stapler of claim 8, wherein the distal end of the locator tube is positioned a distance between about 1 mm and 6 mm from the staple applying member.

10. The surgical stapler of claim 7, wherein the locator tube is slidably disposed within the hollow channel in the shaft.

11. The surgical stapler of claim 7, wherein the locator tube is slidably disposed within a second hollow channel formed in the shaft.

12. The surgical stapler of claim 7, wherein the staple applying member comprises a staple pushing member for advancing at least one staple toward the distal end of the shaft, and an anvil effective to deform a staple to close at least a portion of a puncture in a blood vessel.

* * * * *